(12) United States Patent
Shah et al.

(10) Patent No.: US 8,137,715 B2
(45) Date of Patent: Mar. 20, 2012

(54) INSECTICIDAL COMPOSITION

(75) Inventors: Sujay Anil Shah, London (GB); Christopher William Horsler, Southampton (GB)

(73) Assignee: Livie Biopesticides Limited, London (GB)

( * ) Notice: Subject to any disclaimer, the term of this patent is extended or adjusted under 35 U.S.C. 154(b) by 339 days.

(21) Appl. No.: 12/375,533

(22) PCT Filed: Jul. 30, 2007

(86) PCT No.: PCT/GB2007/002881
§ 371 (c)(1),
(2), (4) Date: Mar. 10, 2009

(87) PCT Pub. No.: WO2008/035029
PCT Pub. Date: Mar. 27, 2008

(65) Prior Publication Data
US 2009/0263511 A1    Oct. 22, 2009

(30) Foreign Application Priority Data

Aug. 3, 2006  (GB) .................................. 0615475.1
Feb. 15, 2007 (GB) .................................. 0702915.0

(51) Int. Cl.
*A61K 36/00* (2006.01)
(52) U.S. Cl. ....................................................... 424/776
(58) Field of Classification Search ........................ None
See application file for complete search history.

(56) References Cited

U.S. PATENT DOCUMENTS

| | | | |
|---|---|---|---|
| 5,645,845 A | 7/1997 | Neumann et al. | |
| 6,296,865 B1 | 10/2001 | Dujardin et al. | |
| 6,835,719 B2* | 12/2004 | Parker et al. | 514/65 |
| 6,849,614 B1 | 2/2005 | Bessette et al. | |
| 2002/0022043 A1 | 2/2002 | Miller | |
| 2005/0038094 A1* | 2/2005 | Warrington | 514/383 |
| 2005/0244445 A1 | 11/2005 | Anderson | |

FOREIGN PATENT DOCUMENTS

| | | |
|---|---|---|
| CN | 1647644 A | 8/2005 |
| CN | 1647645 A | 8/2005 |
| CN | 1792154 A | 6/2006 |
| CN | 1806550 A | 7/2006 |
| DE | 3717467 A1 | 12/1988 |
| DE | 3733640 A1 | 4/1989 |
| DE | 19824681 A1 | 12/1999 |
| EP | 1634500 A2 | 3/2006 |
| FR | 2071322 A | 9/1971 |
| IN | 188378 A1 | 9/2002 |
| JP | 62-114904 A | 5/1987 |
| JP | 2006257050 A1 | 9/2006 |
| WO | 9639034 A1 | 12/1996 |
| WO | 0005964 A1 | 2/2000 |
| WO | 0160163 A2 | 8/2001 |
| WO | 02089584 A1 | 11/2002 |
| WO | 2006055029 A1 | 5/2006 |
| WO | 2006064511 A1 | 6/2006 |
| WO | 2006066152 A2 | 6/2006 |
| WO | 2008011054 A2 | 1/2008 |
| WO | 2008015413 A2 | 2/2008 |
| WO | 2008035029 A2 | 3/2008 |

OTHER PUBLICATIONS

DW ACC 2006-522510, Jul. 2006, Derwent and WO2, Linder et al.*
Ahmed, S. et al., "Stabilization of Pyrethrins for Prolonged Residual Toxicity", "Pyrethrum Post", 1976, pp. 82-88, vol. 13, No. 3.
Bestmann, H. et al., (Abstract Only), "Plant Insecticides. III. Pyrethrin I in the essential oil of *Chrysanthemum balsamita* L", "Zeitschrift fur Naturforschung. C, A journal of biosciences", 1986, pp. 725-728, vol. 41, No. 7-8; Published in German.
Dong, Y. et al., (Abstract Only), "Analysis of chemical components in volatile oils from Rhizoma Chuanxiong by GS-MS", "Shizhen Guoyi Guoyao Bianweihui", 2006, p. 555, vol. 17, No. 4.
Handa, S. et al., (Abstract Only), "Evaluation of dill apiole and dihydrodill apiole as synergists for pyrethrins in dust formulations", "Pyrethrum Post", 1975, pp. 45-46, vol. 13, No. 2.
Kumar, A. et al., "Secondary metabolites of *Chyrsanthemum* genus and their biological activities", Nov. 10, 2005, pp. 1489-1501, vol. 89, No. 9.
Lichtenstein, P. et al., (Abstract Only), "Insecticidal and synergistic components isolated from dill plants", "Journal of Agriculture and Food Chemistry", 1974, pp. 658-664, vol. 22, No. 4.
Meheshwari, M. et al., "Novel Methylenedioxyphenyl Synergists for Pyrethrum and Carbamate Insecticides From Dillapiole", "Indian Perfumer", 1978, pp. 155-160, vol. 22, No. 3.
Reddy, M. et al., "Characterization and Use of Essential Oils From *Thymus vulgaris* Against *Botrytis cinerea* and *Rhizopus stolonifer* in Strawberry Fruit", "Phytochemistry", 1998, pp. 1515-1520, vol. 47, No. 8.
Bylaite, Egle, et al., "Composition of Essential Oil of Costmary [*Balsamita major* (L.) Desf.] at Different Growth Phases", "J. Agric. Food Chem.", 2000, pp. 2409-2414, vol. 48.
Janmaat, Alida F., et al., "Enhanced fumigant toxicity of p-cymene against *Frankliniella occidentalis* by simultaneous application of elevated . . . ", "Pest Management Science", 2001, pp. 167-173, vol. 58.
Juven, B.J., et al., "Factors that interact with the antibacterial action of thyme essential oil and its active constituents", "Journal of Applied Bacteriology", 1994, pp. 626-631, vol. 76.
Regnault-Roger, Catherine, et al., "Fumigant toxic activity and reproductive inhibition induced by monoterpenes on *Acanthoscelides obtectus* (Say) . . . ", "Journal of Stored Products Research", 1995, pp. 291-299, vol. 31, No. 4.
Tunaz, H., et al., "Insect Growth Regulators for Insect Pest Control", "Turk J Agric For", 2004, pp. 377-387, vol. 28.

* cited by examiner

*Primary Examiner* — Christopher R Tate
*Assistant Examiner* — Randall Winston
(74) *Attorney, Agent, or Firm* — Hultquist, PLLC; Steven J. Hultquist; Kelly K. Reynolds (57) ABSTRACT

The use of dill oil or a mixture of two or more components thereof as a potentiator for a pesticide, such as an insecticide and in particular a pyrethroid is described, together with compositions containing dill oil, and their use in agriculture and in veterinary applications.

14 Claims, 6 Drawing Sheets

INSECTICIDAL COMPOSITION

CROSS-REFERENCE TO RELATED APPLICATIONS

This application is a U.S. national phase under the provisions of 35 USC §371 of International Application No. PCT/GB07/02881 filed Jul. 30, 2007, which in turn claims priority of Great Britain Patent Application No. 0615475.1 filed Aug. 3, 2006, and Great Britain Patent Application No. 0702915.0 filed Feb. 15, 2007. The disclosures of such international application and Great Britain priority applications are hereby incorporated herein by reference in their respective entireties, for all purposes.

The present invention relates to the use of dill oil, or combinations of components or fractions thereof as a potentiator for insecticides, in particular for pyrethrin insecticides, as well as to pesticidal compositions comprising dill oil and methods of using them.

Pyrethrum is a highly effective pesticide which has been used for centuries against all manner of insect pests. Pyrethrum is a natural plant oil that is present in the pyrethrum daisy, Chrysanthemum (*Tanacetum cineraria efolium*), a member of the chrysanthemum family. It is found mainly in tiny oil containing glands on the surface of the seed case in the tightly packed flower head and is the plant's own insecticide that it has evolved to keep insects away. Pyrethrum is made up of six complex chemical esters known as pyrethrins, which work in combination to repel and kill insects. Pyrethrum is a unique pesticide in that, used correctly, it is safe for use near humans and warm blooded animals, for example in kitchens and restaurants, food processing factories and other sensitive environments.

Many synthetic insecticides based to some extent upon the chemical structure of the pyrethrins have been developed and these are known as pyrethroids. For the avoidance of doubt, as used herein the expression "pyrethrin insecticide" or "pyrethrin insecticides" includes both pyrethrins (which may be synthetic or obtained from natural sources), and pyrethroids which are the synthetic insecticides.

Piperonyl butoxide is a potentiator that has been commonly used to potentiate the activity of the pyrethrin insecticides against susceptible and resistant insect species. Piperonyl butoxide acts by inhibiting enzymes, mixed function oxidases, which are present in susceptible and more so in pyrethrin and some carbamate resistant insects and hence allows the pyrethrins to be effective.

One of the most important problems associated with pyrethrins is that resistance is already beginning to be found in many insect species in several parts of the world. Pyrethrin resistance, caused either by specific detoxification enzymes or an altered target site mechanism (kdr-type mutations in the sodium channels), has been reported in most continents. If resistance continues to develop and spread at the current rate, it may render such insecticides ineffective in their current form in the not too distant future. Such a scenario would have potentially devastating consequences particularly in public health terms, since they are yet no obvious alternatives to many of the uses of pyrethrins.

Furthermore, one of the most important problems associated with piperonyl butoxide is its toxicity. Its use as a potentiator has been banned in several countries.

Therefore, it is necessary to develop new and effective pesticides and to develop new potentiators for pesticides and particularly for pyrethrin insecticides.

Accordingly, it would, therefore, be desirable to provide a new and effective pesticide which gives high insect mortality following rapid knockdown, and has low mammalian toxicity, low residual activity, low cost, no existing resistance in target pest species and the low possibility of future resistance developing.

It would also be desirable to provide a new potentiator for pesticides and in particular pyrethrin insecticides which is safe and effective to use.

Dill, *Anethum graveolens* L., an annual or biennial herb native to Europe and South-western Asia, is naturalized to North America and the West Indies. Also known as common dill, American dill, European dill and Danish dill. Principal dill production areas are India and Pakistan but Egypt, Fiji, Mexico, the Netherlands, the United States of America, England, Hungary, Germany and Holland also have commercially productive areas. The plant grows erect and can reach a height of one meter. It is characterised by hollow stems, blue-green leaves, and yellow-flowering compound umbels, which produce a dried ripe fruit commonly called seeds.

The essential oils of dill differ in flavour and odour depending upon whether they are obtained from mature seed or dill weed. The seed oil resembles the essential oil of caraway because of the high carvone content (reaching 50 to 60 percent) in mature seeds. Dill seed oil includes d-carvone, d-limonene, d-phellandrene, $\alpha$-pinene, diterpene, d-dihydrocarvone, $\alpha$-phellandrene, $\beta$-pinene, 1,8-cineole, $\beta$-myrcene, para-cymene, thujone ($\alpha$-thujone and $\beta$-thujone) and dillapiole. Dill herb oil contains d-phellandrene, terpinene, limonene, carvone, dillapiole, isomyristicin, and myristicin. As used herein, the expression "dill oil" includes both dill herb oil and/or dill seed oil.

Indian dill, *Anethum sowa*, is a perennial herb grown and utilised similarly to dill. Indian dill has a higher specific gravity than common dill, and is more pungent than European and American varieties, attributed to the presence of dillapiole and a lower carvone content. The composition of Indian dill oil is 60% D-carvone, 35% dillapiole and 5% other oils.

It is known that dillapiole when isolated from the dill oil obtained from *Anethum sowa*, and when further converted to the dihydro derivative by the process of hydrogenation has synergistic activity towards pyrethrins when used as an insecticide in a ratio of 1:5 pyrethrin:dillapiole (Maheshwari et al., Indian Perfumer, Vol XXII 3 (1978) p 155-160). The process of separating dillapiole from dill oil is very expensive and time consuming. Attempts to stabilize pyrethrins for prolonged residual toxicity by combining them with a range of essential oils, including dill oil has also be attempted (S. M. Ahmed et al., Pyrethrum Post, 13(3) 1976, 82-88). Although success with some oils was reported, no stabilization effects with dill oil were noted.

It has been surprisingly found that dill oil as such can be used as an effective as a potentiator for pesticides at ratios as low as 1:6 (equivalent to a ratio of pesticide:dillapiole of about 1:2). It seems clear therefore that dill oil contains components other than dillapiole which assist in this effect. In a first aspect the present invention provides the use of dill oil or a mixture of two or more components thereof, as a potentiator for a pesticide.

Potentiators can be applied so that they may enhance the effect of the pesticide. In doing so, either better pesticidal results may be achieved or the amount of pesticide used may be reduced. Alternatively, the potentiator may reduce or prevent the development of resistance to the pesticide by the target pest.

Particular examples of pesticides whose effect may be enhanced by the use of dill oil or a mixture of two or more components thereof include pyrethrin insecticides as defined herein, as well as carbamate, insect growth regulators, rotenone, and some organophosphates. In particular however, the pesticide is a pyrethrin insecticide.

When used as a potentiator, the dill oil may be applied either simultaneously or sequentially with the pesticide. When applied sequentially, it may be applied in separate operations, for example by sequential spraying operations. For example, in some situations, it may be advisable to apply dill oil in advance of the pesticide, to provide the best possible results. Clearly however, this may be time consuming and labour intensive, and therefore it is preferable to apply the dill oil or mixture of two or more components thereof and the pesticide simultaneously.

For this purpose, it is convenient for the dill oil or mixture of two or more components thereof and the pesticide to be administered in the same composition.

According to a second aspect of the invention, there is provided a pesticidal composition comprising a pesticide (such as a pyrethrin insecticide) and dill oil or mixture of two or more components thereof.

In a particular embodiment, the composition may comprise the individual elements in a manner in which their availability is different. In particular for example, the dill oil or mixture of two or more components thereof may be arranged in a rapid-release formulation, whilst the pesticide may be arranged in a non-rapid release formulation. In this way, the administration of a single composition will result in the administration of the dill oil in advance of the pesticide, which may be beneficial in terms of the potentiator effect achievable. Examples of formulations of this type are disclosed for example in WO03/092378, the entire content of which is incorporated herein by reference.

The ratio of pesticide:dill oil or a mixture of two or more components thereof in the composition will vary depending upon the particular nature of the pesticide and with the precise mixture of components.

In a third aspect, the present invention provides a method for the control of pests which comprises administering to the pest or its environment a pesticidally effective amount of a combination of dill oil or a mixture of two or more components thereof and a pesticide. The combination is suitably administered together, for example by the use of a pesticidal composition of the second aspect of the present invention.

In a fourth aspect the present invention provides a method for the control and/or eradication of pest infestations of animals and/or of plants, and/or stored products which comprises administering to the animal or locus an effective amount of a combination of dill oil or a mixture of two or more components thereof and a pesticide. Again, the combination is suitably administered together, for example by the use of a pesticidal composition of the second aspect of the present invention.

In a fifth aspect, the present invention provides pesticidal compositions of the second aspect of the present invention for use in human and veterinary medicine, in public health control and in agriculture for the control of pests.

In a fifth aspect the present invention provides the use of the compositions of the second aspect of the present invention as a pesticide.

The present inventors have also found that alkyl polyglycosides such as alkyl polyglucosate are particularly effective surfactants in pesticidal compositions such as those comprising dill oil and a pyrethrin insecticide.

Accordingly, the use of alkylpolyglycoside such as alkylpolyglucosate as a surfactant in pesticidal compositions comprising dill oil such as those of the second aspect which further comprise a pesticide such as a pyrethrin insecticide, is particularly preferred.

As used herein, the expression "alkylpolyglycoside" refers to compounds comprising alkyl moities, for example of from 1 to 20 carbon atoms, which are substituted by more than one monosaccharide group, such as glucoside. The alkyl moiety may be straight chain or branched. It suitably comprises from 6 to 15 carbon atoms, and preferably from 8 to 10 carbon atoms.

The present inventors have also found that ethyl lactate is a surprisingly effective solvent in pesticidal compositions, in particular those comprising dill oil and a pyrethrin insecticide.

Accordingly, ethyl lactate may be used as a solvent in pesticidal compositions such as those comprising dill oil or a mixture of at least two components thereof, such as those which further comprise a pesticide such as a pyrethrin insecticide, in accordance with the second aspect of the invention.

The present invention will now be further described. In the following passages different aspects of then invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Parts, proportions and percentages in this specification are by weight unless otherwise indicated.

Dill oil or a mixture of two or more components thereof may be present in the composition in an amount of from about 3% w/w to about 40% w/w, preferably from about 3% w/w to about 12% w/w, even more preferably from about 5% to about 8% w/w and most preferably about 7.7% w/w.

As outlined above there are various varieties of dill oil, Dill, *Anethum graveolens* L. and Dill, *Anethum sowa*. Preferably the dill oil used is Dill, *Anethum sowa*. It may comprise dill seed oil or dill herb oil or a mixture of two or more components thereof, but is preferably a dill seed oil.

The quality of the dill seed oil is dependent on the quality of *Anethum sowa* or *Anethum graveloens* L. *Anethum sowa*, for example, is sensitive to environmental factors such as moisture, temperature and oil condition. Preferably the dill oil is such that it comprises from about 50% to about 65% D-carvone. Such quantities of D-carvone enables a high dillapiole content to be present.

When a mixture of two or more components of dill oil is used, the components are suitably selected so that they provide synergistic effects when used in combination at potentiators. These may be tested using routine procedures.

In a particular embodiment, the mixture will comprise at least two members of the group selected from d-carvone, d-limonene, α-phellandrene, α-pinene, diterpene, d-dihydrocarvone, β-phellandrene, β-pinene, 1,8-cineole, β-myrcene, para-cymene and d-phellandrene, terpinene, limonene, carvone, dillapiole, isomyristicin, and myristicin.

Suitably at least one of the components is dillapiole, and the mixture further comprises one or more of the group selected from d-carvone, limonene, α-phellandrene, α-pinene, diterpene, d-dihydrocarvone, β-phellandrene, β-pinene, 1,8-cineole, β-myrcene, p-cymene, thujone α-thujone and β-thujone) terpinene, isomyristicin, and myristicin.

In an alternative embodiment, at least one of the components is d-carvone, and the mixture further comprises one or more of the group is selected from dillapiole, limonene, α-phellandrene, α-pinene, diterpene, d-dihydrocarvone, β-phellandrene, β-pinene, 1,8-cineole, β-myrcene, p-cymene, thujone (α-thujone and β-thujone) terpinene, isomyristicin, and myristicin.

In yet a further embodiment, at least one of the components is limonene, and the mixture further comprises one or more of the group is selected from d-carvone, dillapiole, α-phellandrene, α-pinene, diterpene, d-dihydrocarvone, β-phellandrene, β-pinene, 1,8-cineole, β-myrcene, p-cymene, thujone (α-thujone and β-thujone) terpinene, isomyristicin, and myristicin.

In particular the mixture further comprises at least two members of the group selected from dillapiole, d-carvone or liminone.

Particular examples of mixtures which may be used as potentiators are mixtures comprising:
1) Dillapiole and d-carvone;
2) Dillapiole and limonene;
3) D-carvone and limonene;
4) Dillapiole, limonene and d-carvone
5) Dillapiole and p-cymene;
6) Dillapiole, limonene and p-cymene;
7) D-carvone and p-cymene;
8) Dillapiole, D-carvone and p-cymene; and
9) D-carvone, limonene and p-cymene.

The ratios of the components in the mixture may be selected so that the mixture provides a good potentiator effect when the mixture is used, for example in combination with a pyrethrin insecticide and these can be determined using routine optimization methods. In particular however, the relative amounts may be selected so that they reflect the ratios in which they appear in dill oil.

In a particular embodiment of all aspects of the invention, dill oil is used in its entirety.

In a particular embodiment, the pesticidal compositions of the present invention further comprise pyrethrin insecticides. When the pyrethrin insecticides are combined with the dill oil or a mixture of at least two components thereof, the dill oil increases the insecticidal activity of the pyrethrin insecticides.

The pyrethrin insecticide may be a natural or synthetic pyrethrin, as well as a pyrethroid. Examples include:
Examples include:
Pyrethrin I (the pyrethrolone ester of chrysanthemic acid);
Cinerin I (the cinerolone ester of chrysanthemic acid);
Pyrethrin II (the pyrethrolone ester of pyrethric acid);
Cinerin II (the cinerolone ester of pyrethric acid);
Jasmolin I (the jasmololone ester of chrysanthemic acid);
Jasmolin II (the Jasmololone ester of pyrethric acid);
Allethrin (2-allyl-4-hydroxy-3-methyl-2-cyclopenten-1-one ester of 2,2-dimethyl-3-(2-methylpropenyl)cyclopropanecarboxylic acid);
Barthrin (6-chloropiperonyl 2,2-dimethyl-3-(2-methylpropenyl) cyclopropane carboxylate;
Dimethrin (2,4-dimethylbenzyl 2,2-dimethyl-3-(2-methylpropenyl) cyclopropane carboxylate;
Tetramethrin (1-cyclohexene-1,2-dicarboximidomethyl 2,2-dimethyl-3-(2-methylpropenyl)cyclopropane carboxylate);
Resmethrin (5-benzyl-3-furylmethyl-cis, transchrysanthemate) and
Bioresmethrin (5-benzyl-3-furylmethyl-transchrysanthemate).
Further examples of specifically pyrethroids include:
Cypermethrin ((S,R)-alpha-cyano-3-phenoxybenzyl-2,2-dimethyl (1R,1S, cis, trans)-3-(2,2-dichlorovinyl)cyclopropane-carboxylate);
Cyphenothrin (RS)-α-cyano-3-phenoxybenzyl (1RS,3RS; 1RS,3SR)-2,2-dimethyl-3-(2-methylprop-1-enyl)cyclopropanecarboxylate);
Empenthrin ((E)-(RS)-1-ethynyl-2-methylpent-2-enyl (1RS, 3RS;1RS,3SR)-2,2-dimethyl-3-(2-methylprop-1-enyl)cyclopropanecarboxylate);
Tralomethrin ((S)-α-cyano-3-phenoxybenzyl (1R,3S)-2,2-dimethyl-3-[(RS)-1,2,2,2-tetrabromoethyl]cyclopropanecarboxylate);
Fenvalerate ((RS)-α-cyano-3-phenoxybenzyl (RS)-2-(4-chlorophenyl)-3-methylbutyrate;
Esfenvalerate ((S)-α-cyano-3-phenoxybenzyl(S)-2-(4-chlorophenyl)-3-methylbutyrate);
Permethrin (including trans-permethrin);
Bioallethrin-((RS)-3-allyl-2-methyl-4-oxocyclopent-2-enyl (1R,3R)-2,2-dimethyl-3-(2-methylprop-1-enyl)cyclopropanecarboxylate) such as S-bioallethrin;
Dimethfluthrin (2,3,5,6-tetrafluoro-4-(methoxymethyl)benzyl (1RS,3RS;1RS,3SR)-2,2-dimethyl-3-(2-methylprop-1-enyl)cyclopropanecarboxylate);
Flucythrinate ((RS)-α-cyano-3-phenoxybenzyl(S)-2-(4-difluoromethoxyphenyl)-3-methylbutyrate);
Fluvalinate ((RS)-α-cyano-3-phenoxybenzyl N-(2-chloro-α, α,α-trifluoro-p-tolyl)-DL-valinate);
Furethrin ((RS)-3-furfuryl-2-methyl-4-oxocyclopent-2-enyl (1RS,3RS;1RS,3SR)-2,2-dimethyl-3-(2-methylprop-1-enyl)cyclopropanecarboxylate);
Imiprothrin (mixture of 20% 2,5-dioxo-3-prop-2-ynylimidazolidin-1-ylmethyl (1R,3S)-2,2-dimethyl-3-(2-methylprop-1-enyl)cyclopropanecarboxylate and 80% 2,5-dioxo-3-prop-2-ynylimidazolidin-1-ylmethyl (1R,3R)-2,2-dimethyl-3-(2-methylprop-1-enyl) cyclopropanecarboxylate);
Metofluthrin (2,3,5,6-tetrafluoro-4-(methoxymethyl)benzyl (EZ)-(1RS,3RS;1RS,3SR)-2,2-dimethyl-3-prop-1-enyl-cyclopropanecarboxylate);
Kadethrin (5-benzyl-3-furylmethyl(E)-(1R,3S)-2,2-dimethyl-3-(2-oxothiolane-3-indenemethyl)-cyclopropanecarb oxylate);
Tetramethrin (cyclohexene-1,2-dicarboximidomethyl (1RS)-cis,trans-2,2-dimethyl-3-(2-methylpropenyl)cyclo-propanecarboxylate);
Phenothrin (3-phenoxybenzyl (1RS,3RS;1RS,3SR)-2,2-dimethyl-3-(2-methylprop-1-enyl)cyclopropanecarboxylate);
Prallethrin ((RS)-2-methyl-4-oxo-3-prop-2-ynylcyclopent-2-enyl (1RS,3RS;1RS,3SR)-2,2-dimethyl-3-(2-methylprop-1-enyl)cyclopropanecarboxylate);
Profluthrin (2,3,5,6-tetrafluoro-4-methylbenzyl (EZ)-(1RS, 3RS;1RS,3SR)-2,2-dimethyl-3-prop-1-enylcyclopropanecarboxylate);
Pyresmethrin (5-benzyl-3-furylmethyl(E)-(1R,3R)-3-(2-methoxycarbonylprop-1-enyl)-2,2-dimethylcyclopropanecarboxylate);
Cismethrin (5-benzyl-3-furylmethyl (1R,3S)-2,2-dimethyl-3-(2-methylprop-1-enyl)cyclopropanecarboxylate);
Tefluthrin (2,3,5,6-tetrafluoro-4-methylbenzyl (1RS,3RS)-3-[(Z)-2-chloro-3,3,3-trifluoroprop-1-enyl]-2,2-dimethyl-cyclopropanecarboxylate);
Proparthrin/Kikuthrin (2-methyl-5-(2-propynyl)-3-furylmethyl (1RS) cis and trans-2,2-dimethyl-3-(2-methylprop-1-enyl) cyclopropanecarboxylate;
Biphenthrin ((2-methyl-3-phenyl-phenyl)methyl 3-(2-chloro-3,3,3-trifluoro-prop-1-enyl)-2,2-dimethyl-cyclopropane-1-carboxylate;
Biopermethrin (3-phenoxybenzyl (1R,3S)-3-(2,2-dichlorovinyl)-2,2-dimethylcyclopropanecarboxylate);
Bifenthrin (2-methylbiphenyl-3-ylmethyl (1RS,3RS)-3-[(Z)-2-chloro-3,3,3-trifluoroprop-1-enyl]-2,2-dimethyl-cyclopropanecarboxylate);

Cyfluthrin ((RS)-α-cyano-4-fluoro-3-phenoxybenzyl (1RS, 3RS;1RS,3SR)-3-(2,2-dichlorovinyl)-2,2-dimethylcyclopropanecarboxylate);

Terallethrin ((RS)-3-allyl-2-methyl-4-oxocyclopent-2-enyl 2,2,3,3-tetramethylcyclopropanecarboxylate);

Bromethrin ((5-benzyl-3-furyl)methyl-2(2,2-dibromovinyl)-3,3-dimethylcyclopropanecarboxylate);

Ethanomethrin;

Bioethanomethrin (5-benzyl-3-furylmethyl (1R,3R)-3-cyclopentylidenemethy-2,2-dimethylcyclopropanecarboxylate);

Transfluthrin (2,3,5,6-tetrafluorobenzyl (1R,3S)-3-(2,2-dichlorovinyl)-2,12-dimethylcyclopropanecarboxylate);

Tralocythrin (RS)— α-cyano-3-phenoxybenzyl (1RS and 3RS)-3-(1,2-dibromo-2,2-dichloroethyl)-2,2-dimethylcyclopropanecarboxylate);

Fenpropanate (Cyclopropanecarboxylic acid, 2,2,3,3-tetramethyl-cyano(3-phenoxyphenyl)methyl ester);

Cypothrin (cyano-(3-phenoxyphenyl)-methyl 3,3-spiro-[cyclopropane-1,1-(1H)-indene]-2-carboxylate);

Fenfluthrin (NAK 1654) (2,3,4,5,6-pentafluorobenzyl (1R, 3S)-3-(2,2-dichlorovinyl)-2,2-dimethylcyclopropanecarboxylate);

NAK 1901 (Pentafluorbenzyl (1R, cis)-3-(2,2-dichlorovinyl)-2,2-dimethyl-cyclopropane-carboxylate;

Fenpirithrin (RS)-cyano(6-phenoxy-2-pyridyl)methyl (1RS, 3RS; 1RS,3SR)-3-(2,2-dichlorovinyl)-2,2-dimethylcyclopropanecarboxylate);

Fenpropathrin ((RS)-α-cyano-3-phenoxybenzyl 2,2,3,3-tetramethylcyclopropanecarboxylate);

Prothrin;

Furamethrin;

Proparthrin;

Permethrin (3-phenoxybenzyl (1RS,3RS;1RS,3SR)-3-(2,2-dichlorovinyl)-2,2-dimethylcyclopropanecarboxylate);

Sumithrin (3-phenoxyphenyl)methyl 2,2-dimethyl-3-(2-methylprop-1-enyl)cyclopropane-1-carboxylate);

Acrinothrin ((S)-α-cyano-3-phenoxybenzyl(Z)-(1R,3S)-2,2-dimethyl-3-[2-(2,2,2-trifluoro-1-trifluoromethyl-ethoxycarbonyl)vinyl]cyclopropanecarboxylate);

Cyhalothrin ((RS)-α-cyano-3-phenoxybenzyl (1RS,3RS)-3-[(Z)-2-chloro-3,3,3-trifluoropropenyl]-2,2-dimethylcyclopropanecarboxylate including λ-cyhalothrin, gamma-cyhalothrin and lamba-cyhalothrin;

Cyclethrin ((RS)-3-[(RS)-cyclopent-2-en-1-yl]-2-methyl-4-oxocyclopent-2-en-1-yl (1RS,3RS;1RS,3SR)-2,2-dimethyl-3-(2-methylprop-1-enyl)cyclopropanecarboxylate;

Cycloprothrin (RS)-α-cyano-3-phenoxybenzyl (RS)-2,2-dichloro-1-(4-ethoxyphenyl)cyclopropanecarboxylate);

Deltamethrin ((S)-α-cyano-3-phenoxybenzyl (1R,3R)-3-(2,2-dibromovinyl)-2,2-dimethylcyclopropanecarboxylate;

Etofenprox (2-(4-ethoxyphenyl)-2-methylpropyl 3-phenoxybenzyl ether);

Flufenprox (3-(4-chlorophenoxy)benzyl (RS)-2-(4-ethoxyphenyl)-3,3,3-trifluoropropyl ether);

Halfenprox (2-(4-bromodifluoromethoxyphenyl)-2-methylpropyl 3-phenoxybenzyl ether);

Protrifenbute ((RS)-5-[4-(4-chlorophenyl)-4-cyclopropylbutyl]-2-fluorophenyl phenyl ether); and Silafluofen ((4-ethoxyphenyl)[3-(4-fluoro-3-phenoxyphenyl)propyl](dimethyl)silane).

A mixture of pyrethrin insecticides can also be present. Preferably the pyrethrin insecticide is a natural pyrethrin or a mixture of natural and synthetic pyrethrins. Even more preferably the pyrethrin insecticide is Pyrethrin I or Pyrethrin II or a mixture thereof. However, for some applications, it will be preferable to utilize a synthetic pyrethroid insecticide such as those listed above.

These pyrethrin insecticides form preferred embodiments of the methods of the third and fourth aspects of the invention.

In a preferred embodiment the pesticide, such as the pyrethrin insecticide is present in the composition in an amount of from about 0.5% w/w to about 5% w/w, preferably from about 0.5% w/w to about 2% w/w, and most preferably from about 0.8% w/w.

The proportions of pesticide such as the pyrethrin insecticide to dill oil can vary over a wide range depending on such factors as the particular ingredients employed, the particular locus to be treated, the particular pests to be combated and the particular effect desired, for example whether a long residual period of control is required. Overall, however, the proportions of pesticide to dill oil may be for example (wt % for both components) from about 1:50 to about 40:1, usually from about 1:10 to about 10:1. Preferably the proportions are from about 1:5 to about 5:1, more preferably from about 1:4 to about 1:3, and most preferably about 1:3.6, in particular when the pesticide is a pyrethrin insecticide as described above.

Suitably the composition further comprises one or more surfactants. Surfactants are particularly useful in spray applications. The spray application process for pesticides can be an inefficient process. Droplets sprayed on to crop leaf surfaces may run off the leaves or may not spread sufficiently on the leaf surface. The wetting, retention and spreading of pesticide spray droplets on leaves can be improved by the addition of surfactants to the formulation or to the spray tank mixture. The surfactant reduces the dynamic surface tension between the water droplets and the leaf surfaces and improves the wetting, spreading and retention characteristics. This can have the effect of enhancing the biological activity of the active ingredient and may have the benefit of reducing pesticide dose rates.

Examples of suitable surfactants include alkylpolyglycoside (Agnique™), which itself is made from natural plant extracts, for example vegetable oils and sugars, calcium dodecylbenzene sulfonate, polyoxyethlenated alkyl phenols, sorbitan or sorbitan polyoxyethenlated esters or sodium petroleum sulphonate, Hyoxid X 45, Atlox 3400B, Emulsol MA, Tween 40, Tween 80, Span 40, Unitox 33X and IGSRF-6000 or other surfactants known in the art. These surfactants may be used alone or in combination. The surfactant can comprise a mixture of Tween 40 and Span 40 in a ratio of about 9:1 to about 1:9, preferably about 9:1 or Unitox 33× and IGSRF-6000 in a ratio of about 9:1 to about 1:9, preferably about 9:1.

In a preferred embodiment the surfactant is an alkyl polyglycoside such as alkyl polyglucosate (Agnique).

The surfactant is preferably present in the composition in an amount of from about 5 to about 30% w/w, most preferably in an amount of from 5 to 10% w/w.

Even more preferably the pesticidal composition comprises dill oil or a mixture of at least two components thereof, a pyrethrin insecticide such as a pyrethrin and a polyglycoside such as a polyglucosate (Agnique). Alkyl polyglycoside (Agnique) enhances the activity of the pyrethrin insecticide. Furthermore, the alky polyglycoside increases the spreading not only on the topside of leaves, but also on the underside of leaves where insects may be present.

The composition may also comprise a solvent. Suitable solvents are one or more appropriate solvents selected from, for example, ethyl lactate, cyclohexanone, ceenine, isopropanol, ethanol, aromax, iomax, xylene, silicon/acetone or olive oil. In some instances, natural organic emulsifiers may be preferred, particularly for organic farming applications. Coconut oil such as coconut diethanolamide is an example of such a compound. Palm oil products such as lauryl stearate may also be used.

In a preferred embodiment the solvent is present in an amount of from about 30 to about 60% w/w, preferably in an amount of from about 40 to about 50% w/w.

In a preferred embodiment the solvent is ethyl lactate. More preferably the pesticidal composition comprises dill oil or a mixture of two or more components thereof, pyrethrin and ethyl lactate.

Even more preferably the pesticidal composition comprises dill oil or a mixture of two or more components thereof, pyrethrin, ethyl lactate and alkyl polyglycoside such as alkyl polyglucosate.

The pesticidal compositions, and in particular the pesticidal compositions which comprise pyrethrins, can further comprise UV screening agents. Examples of suitable UV screening agents include titanium dioxide and carotene. Preferably, the carotene comprises one or more of α-carotene, β-carotene, γ-carotene, δ-carotene, ∈-carotene, lutein, lycopene and astaxanthin. Astaxanthin and β-carotene are preferred and may be used individually or in combination. Astaxanthin is most preferred and has been found to provide greater protection of UV-sensitive agrochemicals from UV-light. The composition of the present invention may comprise astaxanthin and/or β-carotene.

In a preferred embodiment the UV screening agent is present in the composition in an amount of from about 0.005% w/w to about 50% w/w, preferably from about 0.05% w/w to about 10% w/w, and most preferably from about 1% w/w to 5% w/w.

The ratio of dill oil or a mixture of two or more components thereof to UV Screening agent (wt % for both components) in the composition is preferably 100:1 to 1:100, more preferably 25:1 to 1:5, most preferably, 1:1 to 1:5.

The pesticidal compositions, and in particular the pesticidal compositions which comprise pyrethrins, can further comprise insect growth regulators. Examples of the insect growth regulator which can be used include methoprene, pyriproxyfen, lufenuron, azadirachtin, diofenolan, fenoxycarb, hydroprene, kinoprene, tetrahydroazadirachtin, buprofesin and mixtures thereof. Preferably the insect growth regulator is methoprene and/or pyriproxyfen.

In a preferred embodiment the composition of the present invention is used to control flying and crawling insects.

The present invention provides a method for the control of pests which comprises administering to the pest or its environment a pesticidally effective amount of a pesticidal composition of the present invention.

The present invention also provides a method for the control and/or eradication of pest infestations of animals and/or of plants, (including trees), and/or stored products which comprises administering to the animal or locus an effective amount of a pesticidal composition of the present invention.

The present invention further provides for the pesticidal compositions of the present invention for use in human and veterinary medicine, in public health control and in agriculture for the control of pests.

The methods and pesticidal compositions of the present invention are of particular value in the protection of field, forage, plantation, glasshouse, orchard and vineyard crops, of ornamentals and of plantation and forest trees, for example, cereals (such as maize, wheat, rise, sorghum), cotton, tobacco, vegetables and salads (such as beans, cole crops, lettuce, onions, tomatoes and peppers), field crops (such as potato, sugar beet, ground nuts, soybean, oil seed rape), sugar cane, grassland and forage (such as maize), plantations (such as tea, coffee, cocoa, banana, oil palm, coconut, rubber, spices), orchards and groves (such as of stone and pip fruit; citrus, kiwifruit, mango, avocado, olives and walnuts, vineyards, ornamental plants, flowers and shrubs under glass and in gardens and parks, forest trees (both deciduous and evergreen) in forests, plantations and nurseries.

They are also valuable in the protection of timber (standing, felled, converted, stirred or structural) from attack by saw flies or beetles.

They have applications in the protection of stored products such as grains, fruits, nuts, spices and tobacco, whether whole, milled or compounded into products from moth, beetle and mite attack. Also protected are stored animal products such as skins, hair, wool and feathers in natural or converted form (such as carpets or textiles) from moth and beetle attack; also stored meat and fish from beetle, mite and fly attack.

The methods and pesticidal compositions of the present invention are therefore, useful in the control of arthropods e.g. insects and acarines in any environment where these constitute pests such as in agriculture, in animal husbandry, in public health control and in domestic situations.

Insect pests include whitefly, thrips, termites (Isoptera), cockroaches, flies, aphids (Homoptera), beetles (Coleoptera), bugs, water bugs (Heteroptera), sawflies, wasps, bees and ants (Hymenoptera), mites, midges, moths and butterflies (Lepidoptera), leafhoppers and mosquitoes.

In particular the methods and compositions of the invention are envisaged for the control of the following species of whitefly:

*Trialeurodes vaporariorum* (Glasshouse Whitefly), *Trialeurodes abutilonea, Aleurothirus floccosus, Aleurodicus disperses, Bemisia argentifolia* (Silverleaf Whitefly), *Bemisia tabaci, Bemisia graminus, Pseudaulacaspis pentagona* (White Peach Scale), and in particular *Bemisia tabaci, Bemisia argentifolia, Trialeurodes vaporariorum* and *Pseudaulacaspis pentagons*.

In particular the methods and compositions of the invention are envisaged for the control of the following species of thrips: *Frankliniella occidentalis, Thrips tabaci, Thrips palmi, Scirtothrips aurantii, Scirtothrips citri, Limnothrips cerealium, Haplothrips tritici, Kanothrips robustus, Diarthrothrips coffeae, Taenothrips inconsequeus, Taenothrips simplex, Heterothrips azaleae, Liothrips oleae* and *Heliothrips haemorhoidalis* and in particular *Frankliniella occidentalis, Thrips tabaci* and *Thrips palmi*.

In particular the methods and compositions of the invention are envisaged for the control of the following species of termites (Isoptera): Arid-land subterranean termite, common dry-wood termite, damp-wood termite, dry-wood termite, eastern subterranean termite, Formosan subterranean termite, pacific damp-wood termite, south-eastern dry-wood termite, southern dry-wood termite, subterranean termite, tree termite, western dry wood termite and western subterranean termite.

In particular the methods and compositions of the invention are envisaged for the control of the following species of cockroaches:

Madagascar cockroach, American cockroach, brown-banded cockroach, German cockroach, oriental cockroach, smoky-brown cockroach, woods cockroach, Australian cockroach, brown cockroach, Surinam cockroach and Florida woods cockroach.

In particular the methods and compositions of the invention are envisaged for the control of the following species of fly: House fly, sand fly, stable fly and tsetse fly.

In particular the methods and compositions of the invention are envisaged for the control of the following species of aphid (Homoptera): *Aphis fabae* (Black Bean Aphid), *M. persicae* (Peach potato aphids), *Acyrthosiphum pisum* (Pea Aphid), *Brevicoryne brassicae* (Cabbage Aphid), *Sitobion avenae* (Grain Aphid), *Cavariella aegopodii* (Carrot Aphid), *Aphis craccivora*

(Groundnut Aphid), *Aphis gossypii* (Cotton Aphid), *Aphis nasturii*, *Aphis idaei*, *Aphis citricol*, *Toxoptera aurantii* (Black Citrus Aphid), *Drepanoiphum platanoides*, *Myzus persicae*, *Myzus ascalonicas*, *Myzus ornatus*, *Rhopalosiphum padi*, and *Metapolophium dirhodum*. Particular examples are *Myzus persicae* and *Aphis fabae*.

In particular the methods and compositions of the invention are envisaged for the control of the following species of beetle (Coleoptera): Mealworm beetle, *Monochamus alternatus* (Japanese pine sawyer), Rosemary leaf beetle, Asparagus beetle, Red Lily beetle.

In particular the methods and compositions of the invention are envisaged for the control of the following species of bug: Bed bug, redjuv bug, and cone nose bug.

In particular the methods and compositions of the invention are envisaged for the control of the following species of water bugs (Heteroptera): *Dysdercus fasciatus* (cotton stainer)

In particular the methods and compositions of the invention are envisaged for the control of the following species of ants (Hymenoptera): Argentine ant, Big-headed ant, black imported fire ant, brown carpenter ant, cornfield ant, Florida carpenter ant, Imported fire ant, large yellow ant, leaf cutter ant, little black ant, odorous house ant, pavement ant, pharaoh ant, red carpenter ant, red imported fire ant, small yellow ant, southern fire ant, Texas leaf cutting ant and thief ant.

In particular the methods and compositions of the invention are envisaged for the control of the following species of mite: *Panonychus* species such as *Panonychus ulmi* (Red Spider Mite), *Panonychus citri* (Citrus Red Mite), *Tetranychus* species such as *Tetranychus urticae* (Two spotted Spider Mite), *Tetranychus cinnabarinus* (Carmine Spider Mite) *Tetranychus kanzawi* (Kanzawa Spider Mite), *Tetranychus pacificus* (Pacific Spider Mite), *Tetranychus turkestanii* (Strawberry Mite), *Oligonychus* species such as *Oligonychus panacea* (Avocado Brown Mite), *Oligonychus persea* (Persea Mite), *Oligonychus pratensis* (Banks Grass Mite), and *Oligonychus coffeae*, *Aculus* species such as *Aculus cornatus* (Peach Silver Mite), *Aculus fockeni* (Plum Rust Mite) and *Aculus lycopersici* (Tomato Russet Mite), *Eotetranychus* species such as *Eotetranychus wilametti*, *Eotetranychus yumensis* (Yuma Spider Mite) and *Eotetranychus sexmaculatis* (Six Spotted Mite), *Bryobia rubrioculus* (Brown Mite), *Epitrimerua pyri* (Pear Rust Mite), *Phytoptus pyri* (Pear Leaf Blister Mite), *Acalitis essigi* (Red Berry Mite), *Polyphagotarsonemus latus* (Broad Mite), *Eriophyes sheldoni* (Citrus Bud Mite), *Brevipalpus lewisi* (Citrus Flat Mite), *Phylocoptruta oleivora* (Citrus Rust Mite), *Petrobia lateens* (Brown Wheat Mite), *Oxyenus maxwelli* (Olive Mite) and *Diptacis gigantorhyncus* (Bigheaded Plum Mite). Particular examples are *Tetranychus urticae, Tetranychus cinnabarinus, Tetranychus kanzawi, Panonychus ulmi, Panonychus citri* and *Phylocoptruta oleivora*.

In particular the methods and compositions of the invention are envisaged for the control of the following species of moths and butterflies (Lepidoptera): *Lobesia botrana* (European grapevine moth), *Pieris melete* (White butterfly) and *Pieris napi* (Green-veined white butterfly). In particular the methods and compositions of the invention are envisaged for the control of the following three major genera of medically important mosquitoes which transmit diseases, namely *Anopheles, Culex* and *Aedes*, for example *anopheles gambiae, culex quinquefasciatus*, and *aedes aegypti*.

In a preferred embodiment the methods and compositions of the invention are used for the control of whiteflies, thrips, mosquitoes and aphids.

The pesticidal composition of the present invention may be employed alone or in the form of mixtures with such solid and/or liquid dispersible carrier vehicles if desired, or in the form of particular dosage preparations for specific application made there from, such as solutions, emulsions, suspensions, powders, pastes, and granules that are thus ready for use. The pesticidal composition can be formulated or mixed with, if desired, conventional inert diluents or extenders of the type usable in conventional pesticide formulations or compositions, e.g. conventional pesticide dispersible carrier vehicles such as gases, solutions, emulsions, suspensions, emulsifiable concentrates, spray powders, ready-to-use (RTU) micro-emulsions, oil-in-water emulsions, pastes, soluble powders, dusting agents, granules, foams, pastes, tablets, aerosols, natural and synthetic materials impregnated with active compounds, microcapsules, coating compositions, and formulations used with burning equipment, such as fumigating cartridges, fumigating cans and fumigating coils, as well as ULV cold mist and warm mist formulations.

The formulations are preferred to be water soluble or miscible since they are diluted in water before use to achieve an appropriate concentration.

Liquid treatments can be applied by spraying. Formulations include water-soluble powders (SP), soluble (liquid) concentrates, wettable powders (WP) or water-dispersable granules (WG). Solid formulations such as granules or briquettes, where the active ingredient is mixed with bulking agents such as sawdust, sand or plaster, can easily be used by introduction of the formulation into water containers such as tanks or latrines. For the treatment of water, it is of particular benefit to formulate the composition so that the active ingredients will be released slowly over a period of time. This avoids the need for continuous re-treatment.

The composition is preferably formulated as an emulsifiable concentrate (EC). Generally, a 25-50% solution of the insecticide in a solvent is used and at least 10% solubility is typically needed to make the formulation economic to transport. In many cases, insecticides are soluble in organic solvents but not in water. In addition to appropriate solvents, emulsifiers are added to ensure that a fine oil drop (1-2 nm) in water emulsion is produced when the formulation is diluted with water. The resultant emulsion appears opaque and does not settle for 24 hours. ECs are a convenient way of formulating water-insoluble ingredients and they do not cause nozzle abrasion.

Typical solvents for conventional emulsifiable concentrates are non-polar water-immiscible solvents or polar aprotic water miscible organic solvents. These solvents have very low solubilities in water and are capable of dissolving a wide range of active ingredients.

The non-polar solvents are selected from the group consisting of aliphatic or aromatic hydrocarbons and esters of plant oils or mixtures thereof.

Aliphatic and aromatic hydrocarbons such as hexane, cyclohexane, benzene, toluene, xylene, mineral oil or kerosin or substituted naphthalenes, mixtures of mono- and polyalkylated aromatics are, for example, commercially available under the registered trademarks Solvesso, Shellsol, Petrol Spezial and Exxsol.

Esters of plant oils, which are used as nonpolar, water-immiscible solvents according to the present invention are, alkyl esters obtainable from medium chained fatty acids by esterification with alkanols or by transesterification of the corresponding plant oils preferably in the presence of a lipase. Preferred fatty acids of these plant oils have 5 to 20, in particular 6 to 15 carbon atoms. In a preferred embodiment, the methyl ester of the plant oil used is the methyl ester of caprylic/capric ester or of capric ester having a distribution of fatty acid chain lengths around 10 units. Particularly preferred methyl esters of plant oils are Witconol 1095 and Witconol 2309 which are commercially available from the Witco Corporation, Houston, USA.

The water-miscible polar aprotic organic solvents are preferably compounds which exhibit a dielectric constant of 2.5 or more at 25° C., in particular from 2.7 to 4.0 at 25° C. Particularly preferred are cyclic amides and lactones, for example N-methylpyrrolidone, N-cyclohexylpyrrolidone and γ-butyrolactone and N-methylpyrrolidone or mixtures thereof.

Also preferred are water-miscible polar aprotic solvents selected from the group consisting of alkyl lactates, in particular, isopropyl lactate such as plurasolv IPL which is obtainable from Plurac, alky carbonates, polyethylene glycols, polyethylene glycol alkyl ethers, polypropylene glycol alkyl ethers, and most preferably particular isopropyl lactate, or mixtures thereof.

The emulsifiers may comprise at least one emulsifier which can be a non-ionic surfactant, ionic surfactant or a blend of both type of surfactants.

Examples of the nonionic surfactants which can be used include alkoxylate block polymers, alkoxylated alcohols, alkoxylated alkylphenols; alkoxylated amines, alkoxylated amides; alkoxylated fatty esters, alkoxylated oils, fatty esters, alkoxylated fatty acids and sorbitan derivatives. In a preferred embodiment the nonionic surfactants can include alkoxylated alcohols, ethoxylated glycerides and ethoxylated tristyryl. The nonionic emulsifier can be present in the emulsifiable concentrate in an amount of from about 1 to about 15% w/w.

Examples of the ionic surfactants which can be used include: alkylaryl sulfonates; alkylaryl sulfonic acids; carboxylated alcoholethoxylates and alkylphenol ethoxylates; carboxylic acids/fatty acids; diphenyl sulfonate derivatives; olefin sulfonates; phosphate esters; phosphorous organic derivatives; quaternary surfactants; sulfates and sulfonates of oils and fatty acids; sulfates and sulfonates ethoxylated alkylphenols; sulfates of ethoxylated alcohols; sulfates of fatty esters sulfonates of dodecyl and tridecylbenzenes; sulfonates of naphthalene and alkyl naphthalene; sulfonates of petroleum; sulfosuccinamates, alkanolamides and alkoxylated amine. In a preferred embodiment the ionic surfactant can be salts of dodecylbenzene sulfonic acid. The ionic emulsifier can be present in the emulsifiable concentrate in an amount of from about 0.5 to about 10% w/w.

An emulsifiable concentrate can also include an anti-freeze agent. Examples of suitable anti-freeze agents include relatively low molecular weight aliphatic alcohols such as ethylene glycol, propylene glycol, diethylene glycol, glycerine, urea, hexane diol, and sorbitol. Preferred anti-freeze agents include dipropylene glycol, diethylene glycol, glycerine, urea, hexylene glycol and propylene glycol. The anti-freeze agent can be present in the emulsifiable concentrate in an amount of from about 1 to about 10% w/w.

The pesticidal compositions can also be used as ready-to-use (RTU) micro-emulsions. The RTU micro-emulsions can comprise at least one emulsifier, the examples of which are the same as used in emulsifiable concentrates as outlined above. The nonionic emulsifier can be present in the micro-emulsion in an amount of from about 0.002 to about 0.1% w/w. The ionic emulsifier can be present in the micro-emulsion in an amount of from about 0.002 to about 0.1% w/w.

The RTU-micro-emulsions can also include an anti-freeze agent, the examples of which are the same as used in emulsifiable concentrates as outlined above. The anti-freeze agent can be present in the micro-emulsion in an amount of from about 1 to about 10% w/w.

Even more preferably the pesticidal composition comprising dill oil or a mixture of two or more components thereof, a pyrethrin insecticide such as a pyrethrin, ethyl lactate and alkyl polyglycoside (Agnique) such as alkylpolyglucosate is formulated as either an emulsifiable concentrate (EC), an oil-in-water emulsion (EW) or a ready-to-use (RTU) micro-emulsion. In an even more preferred embodiment the composition further comprises an emulsifier and beta carotene.

The pesticidal composition of the present invention is also suited for aerosol-based applications, including aerosolized foam applications. Pressurised cans are the typical vehicle for the formation of aerosols. An aerosol propellant that is compatible with the pesticide composition is used. Preferably, a liquefied-gas type propellant is used. Suitable propellants include compressed air, carbon dioxide, butane and nitrogen. The concentration of the propellant in the insecticide composition is from about 5% to about 40% by weight of the pesticide composition, preferably from about 15% to about 30% by weight of the pesticide composition.

The pesticide formulation can also include one or more foaming agents. Foaming agents that can be used include sodium laureth sulphate, cocamide DEA, and cocamidopropyl betaine. Preferably, the sodium laureth sulphate, cocamide DEA and cocamidopropyl are used in combination. The concentration of the foaming agent(s) in the pesticide composition is from about 10% to about 25% by weight, more preferably about 15% to about 20% by weight of the composition.

When the pesticide formulation is used in an aerosol application not containing foaming agent(s), the composition of the present invention can be used without the need for mixing directly prior to use. However, aerosol formulations containing the foaming agents do require mixing (i.e. shaking) immediately prior to use. In addition, if the formulations containing foaming agents are used for an extended time, they may require additional mixing at periodic intervals during use.

An area may also be treated with the pesticidal composition by using a burning formulation, such as a candle, a smoke coil or a piece of incense containing the composition. For example, composition may be comprised in household products such as "heated" air fresheners in which pesticidal compositions are released upon heating, for example, electrically, or by burning.

Dill oil can be extracted from dill seeds by steam distillation, solvent extraction or super critical extraction.

Steam distillation is the conventional method used. The dill seeds for example are placed in stainless steel vessels with each vessel having a capacity of about 800 to 1000 kg.

Typically 6 to 10 vessels are used. The steam is passed at a high pressure of 7 kg and the dill seed oil is extracted as a distillate using a fractional distillate column. Typically the dill seeds are steam distilled on the day of harvest to minimize volatilisation losses.

On a laboratory scale, the extraction can be carried out as follows:

Steam distillation: Seeds/crushed seeds are subjected to steam distillation for about 12 to about 20 hours. The oil-water mixture collected is extracted thrice with diethyl ether, the ether extract dried over anhydrous sodium sulphate, fused calcium chloride or any other dehydrating agent and the solvent removed to obtain the oil (yield 2 to 2.2%). In place of diethyl ether, dichloromethane or n-hexane (petroleum ether 60 to 80° C.) can also be used.

Solvent extraction, namely cold solvent extraction or hot solvent extraction, as a process for extracting dill oil from dill seeds, was introduced after steam distillation. This process is more expensive than steam distillation but it does give a better yield and quality of oil. One slight limitation is that often traces of the solvent used can be found with the oil.

On a laboratory scale, the extraction can be carried out as follows:

Cold Solvent Extraction: Seeds/crushed seeds/residual seeds from steam distillation may be extracted with cold petroleum ether thrice at room temperature (total about 24 hours). The pooled solvent is filtered and distilled off at low temperature under reduced pressure to obtain dark yellowish brown oil (yield 2.0 to 2.5%). Some fixed oil (0.1 to 0.2%) is also obtained along with the essential oil.

To expedite cold extraction, continuous blending of seeds and solvent mix is recommended.

Holt Solvent Extraction: Extract seeds/crushed seeds/residual seeds from steam distillation in a Soxhlet extractor with hot petroleum ether (approximately 6 hours) ensuring regular frequent solvent siphoning. From the extract, distil off the solvent to obtain greenish yellow coloured oil (yield 2.5 to 3.0%).

Super critical extraction is the latest technology used to extract dill oil from dill seeds. This process uses carbon dioxide as an extracting medium.

The invention will now be described with respect to the following examples. The examples are not intended to be limiting of the scope of the present invention but read in conjunction with the detailed and general description above, provide further understanding of the present invention and an outline of a preferred process for preparing the compositions of the invention.

The examples refer to the accompanying drawings in which.

EXAMPLE 1

EC Formulation

An emulsifiable concentrate formulation was made by dissolving a pyrethrin 50 concentrate, dill seed oil, emulsifier and surfactant in a solvent. Stirring is carried out until all the components have dissolved and a clear solution is obtained.

|  | g/litre |
| --- | --- |
| Refined extract of pyrethrins (50% concentrate) | 97.5 |
| Dill seed oil | 175.0 |
| EO/PO block copolymer | 50.0 |
| Alkyl Polyglycosides | 500.0 |
| Ethyl lactate | to 1 |

EXAMPLE 2

EW Formulation

An oil-in-water emulsion formulation was made by first making a solution of a pyrethrin concentrate, dill seed oil, and surfactant to give a non-aqueous concentrate. A surfactant emulsifier is dissolved in water to give an aqueous concentrate. An emulsion is formed by adding the non-aqueous concentrate to the aqueous concentrate using a high shear mixer to give a homogeneous product.

|  | g/litre |
| --- | --- |
| Refined extract of pyrethrins (50% concentrate) | 97.5 |
| Dill seed oil | 175.0 |
| EO/PO block copolymer | 100.0 |
| Alkyl Polyglycosides | 500.0 |
| Water | to 1 |

EXAMPLE 3

Emulsion Formulation with UV Screening Agent

An oil-in-water emulsion formulation was made by first making a solution of a pyrethrin concentrate, dill seed oil, surfactant and titanium dioxide oil dispersion to give a non-aqueous concentrate. A surfactant emulsifier is dissolved in water to give an aqueous concentrate. An emulsion is formed by adding the non-aqueous concentrate to the aqueous concentrate using a high shear mixer to give a homogeneous product.

|  | g/litre |
| --- | --- |
| Refined extract of pyrethrins (50% concentrate) | 97.5 |
| Dill Seed oil | 175.0 |
| EO/PO block copolymer | 100.0 |
| Alkyl polyglycosides | 500.0 |
| Titanium dioxide 50% oil dispersion | 20.0 |
| Water | to 1 |

EXAMPLE 4

Synergy Studies

Studies have been carried out to determine the synergistic effects of combinations of pyrethrins and dill seed oil using the cereal aphid as a bio-indicator. The formulations prepared were as shown in Tables 1:

TABLE 1

Formulations prepared for testing

| Component | Formulation blank % w/w | Pyrethrin only formulation % w/w |
|---|---|---|
| Pyrethrins (50%) | — | 8.82 |
| Dill Seed Oil | — | — |
| Agnique (adjuvant) | 45.45 | 45.45 |
| Emulsifier | 25.00 (5% w/w emulsifier) | 25.00 (5% w/w emulsifier) |
| Solvent - ethyl lactate | 29.55 | 20.73 |

| Component | Pyrethrin:dill seed oil 1:1 formulation % w/w | Pyrethrin:dill seed oil 1:3 formulation % w/w |
|---|---|---|
| Pyrethrins (50%) | 8.82 | 8.82 |
| Dill Seed Oil | 4.41 | 13.23 |
| Agnique (adjuvant) | 45.45 | 45.45 |
| Emulsifier | 25.00 (5% w/w emulsifier) | 25.00 (5% w/w emulsifier) |
| Solvent - ethyl lactate | 16.32 | 7.50 |

| Component | Pyrethrin:dill seed oil 1:6 formulation % w/w | Pyrethrin:dill seed oil 1:3.6 (field) formulation % w/w |
|---|---|---|
| Pyrethrins (50%) | 8.82 | 8.82 |
| Dill Seed Oil | 26.46 | 15.91 |
| Agnique (adjuvant) | 45.45 | 45.45 |
| Emulsifier | 19.27 (5% w/w emulsifier) | 25.00 (5% w/w emulsifier) |
| Solvent - ethyl lactate | — | 4.82 |

Application

Treatments were applied to the plants using a Potter Laboratory Spray Tower (Burkard Manufacturing Co. Ltd, Rickmansworth, U.K.). The sprayer was calibrated in advance by collecting spray deposits in 9 cm Petri dish bases. The pressure selected was 7.5 p.s.i. According to the calibrations carried out, the mean (n=5) recorded output was 524.0 L/ha (actual range 507.9-544.7 L/ha).

Application Rates

Formulations were sprayed at rates of 1000, 500, 250, and 125 g product/ha. There were two control treatments—plants sprayed with deionised water only and unsprayed plants.

Test Substrate

Barley plants (Var Pearl) were grown in multi-purpose compost, four plants per pot.

Replicates

Three replicate pots were used for each treatment rate.

Test System

Cereal aphids (*Rhopalosiphium padi*) were used and the plants were infested by transferring aphids from stock plants on to the leaves using sections of infested leaf and leaving them in place for the aphids to transfer naturally.

Assessment Timings

The plants were infested with aphids (as described previously) and the numbers of aphids on each replicate leaf counted before application. The numbers of aphids on the leaf were assessed at one and four days after application (DAA).

Maintenance of the Tests

The test was maintained in a controlled environment room at 19.0-22.4° C. with a humidity of 52.3-91.5%. Light intensity was recorded as 5270-6890 Lux.

Data Analysis

The effectiveness of each treatment was determined by the mean number of aphids alive at each assessment time compared to the mean number alive at the start of the test. There was no statistically significant difference (t-test in Excel, one-tailed, P=0.05) in the number of aphids in the unsprayed controls compared to the water only sprayed controls so these values were combined. The numbers of aphids at 4 DAA were then compared for each formulation at each rate by calculating the number of aphids present at 4 DAA as a percentage of the number at the start. The data were tested for normality and for homogeneity of variance using the computer program ToxCalc™ (1999), before carrying out a suitable multiple comparison procedure.

Results: Efficacy of the Formulations

The efficacy of each of the formulations against the cereal aphids is shown in FIGS. 1 to 5 for the formulation blank, pyrethrin only formulation, pyrethrin:dill seed oil 1:1, 1:3, 1:6 and 1:3.6 (field) formulations respectively.

Figure 1:
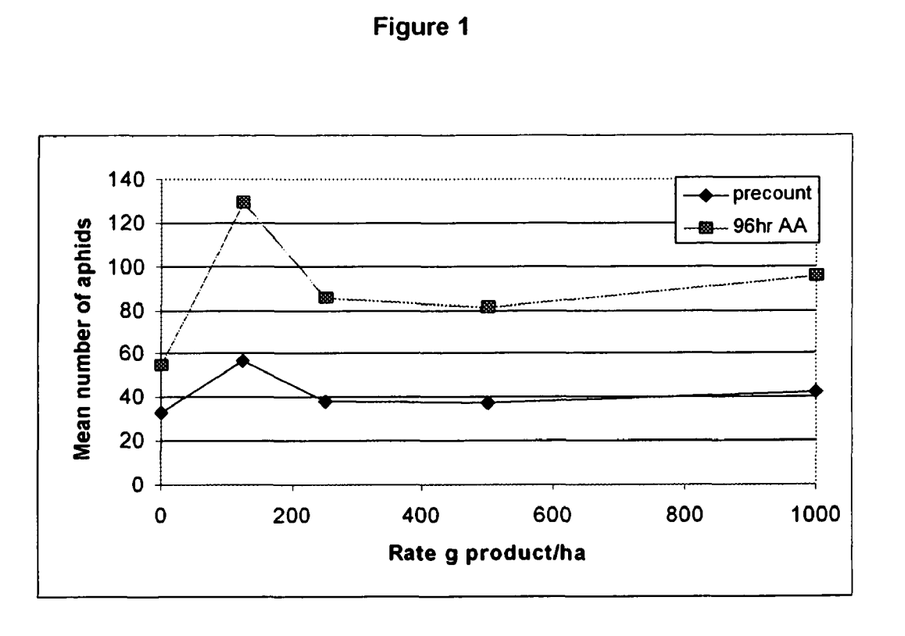
FIG. 1 is a graph showing the efficacy of Formulation Blank against cereal aphids.
Figure 2:
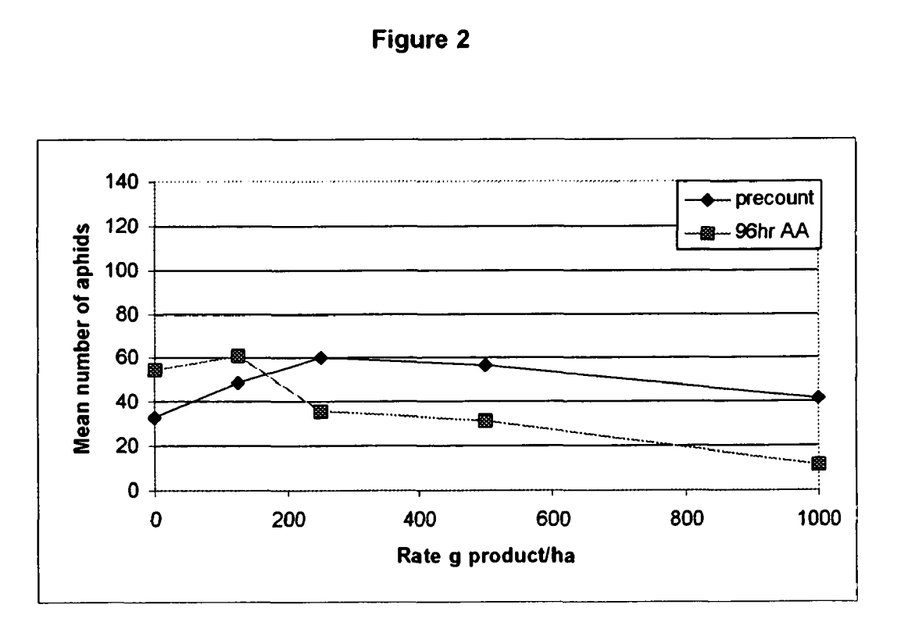
FIG. 2 is a graph showing the efficacy of Pyrethrin Only Formulation against cereal aphids.
Figure 3:
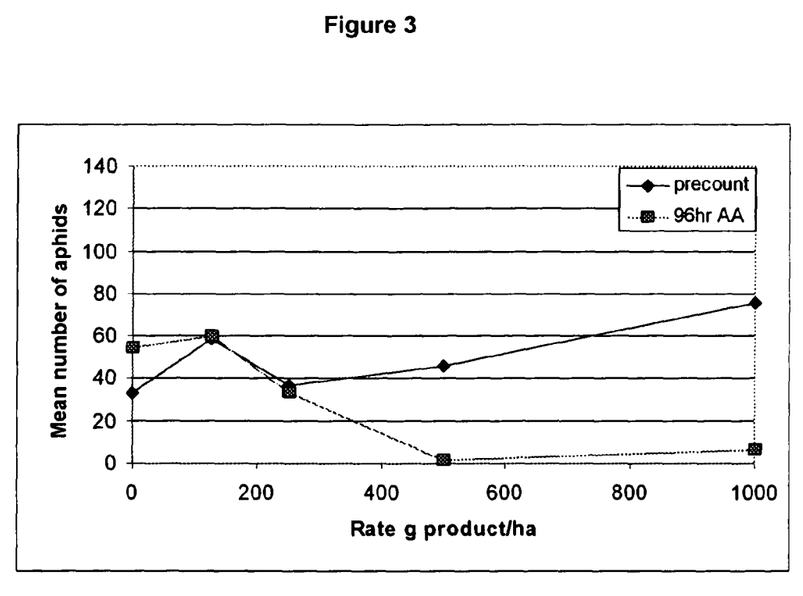
FIG. 3 is a graph showing the efficacy of Pyrethrin:Dill Seed Oil (1:1) Formulation against cereal aphids.
Figure 4:
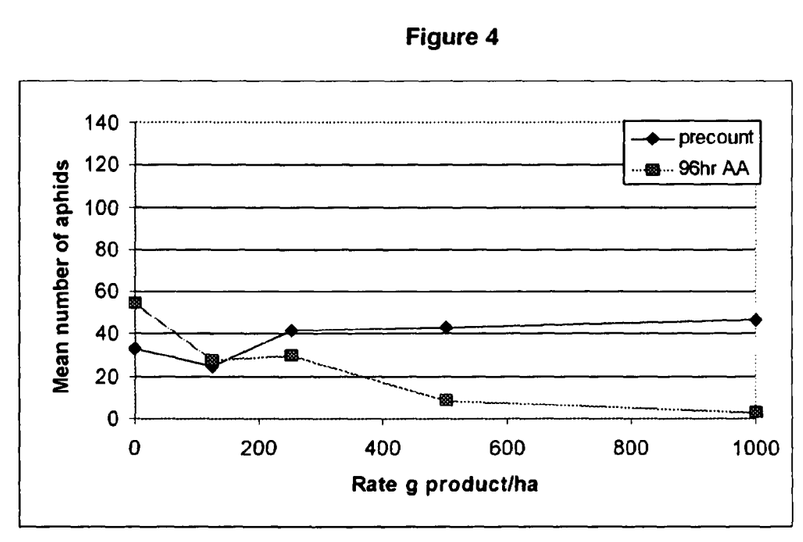
FIG. 4 is a graph showing the efficacy of Pyrethrin:Dill Seed Oil (1:3) formulation against cereal aphids.
Figure 5:
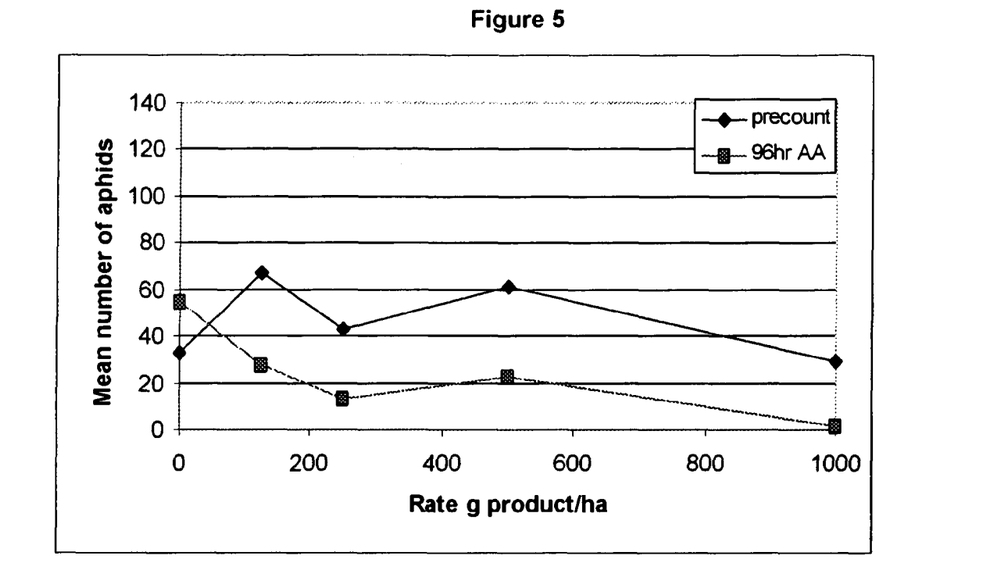
FIG. 5 is a graph showing the efficacy of Pyrethrin:Dill Seed Oil (1:6) Formulation against cereal aphids.
Figure 6:
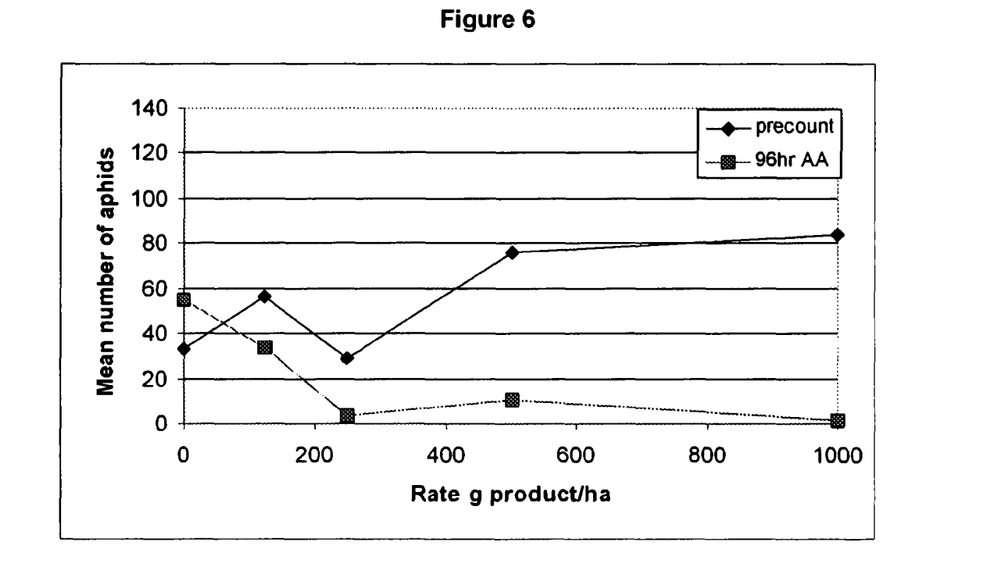
FIG. 6 is a graph showing the efficacy of Pyrethrin:Dill Seed Oil (1:3.6) Field Formulation against cereal aphids.
Figure 7:
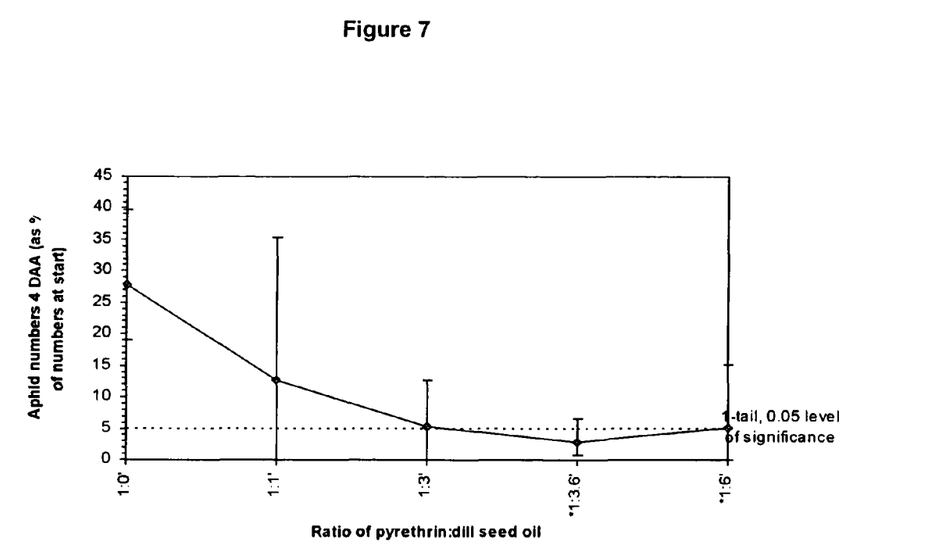
FIG. 7 is a graph showing the synergistic Effects Between Pyrethrin and Dill Seed Oil at 1000 g product/ha.

The synergistic effects of each of the pyrethrin:dill seed oil formulations at each treatment rate were compared statistically. The effects at the 1000 g product/ha rate are shown graphically in FIG. 6. The dotted line is the one-tailed, 0.05 level of significance. Any point below this line is statistically significant and shows an increased level in aphid control.

These results show that synergism existed between pyrethrin and dill seed oil using cereal aphids as a bio-indicator with an optimum ratio of 1:3.6.

EXAMPLE 5

Field Efficacy Studies

Field trials have been undertaken during 2006 against a range of pests on bell peppers (*Capsicum annuum*) and tomatoes (*Lycopersicon esculentum*) using different EW formulations of the product. Product containing 3.03, 6.06, 12.1, 24.2 and 48.5 g/l of pyrethrins plus dill oil in a ratio of 1:3.6 have been applied. Trials have been undertaken to GEP with four replicates, a randomised complete block design with plots 6 m×1 m, and an application volume of 300 L/ha. The key pest species tested was the whitefly, *Bemisia tabaci* (juveniles and adults). Assessments were made pre-treatment and 1, 2, 4, 7 and 14 days after application, with whitefly being assessed by counting the number of adults and larvae (nymphs) on 25 leaves/plot. The early assessments provide information on knock-down while assessments from 4-14 days after application provide data regarding persistence and re-infestation.

Figure 8:
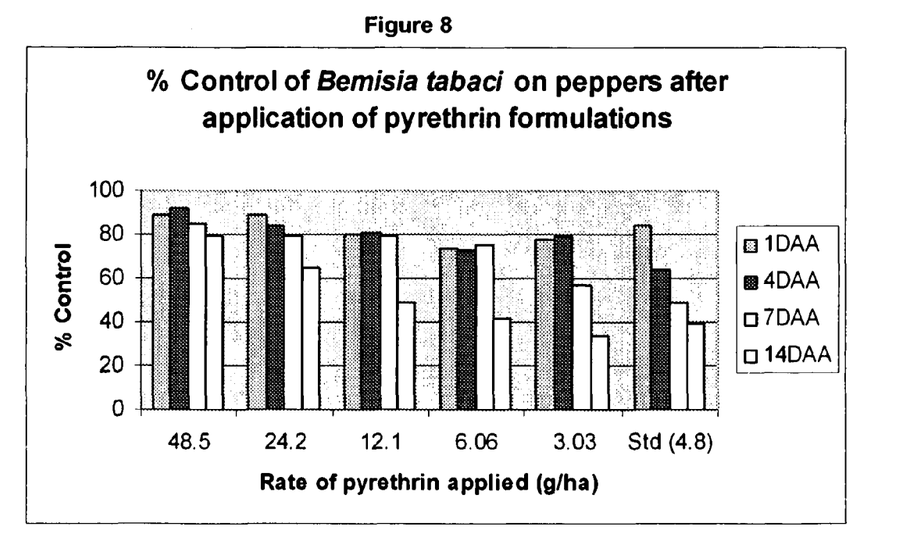
FIG. 8 is a graph showing the effect of the bio-insecticide/acaricide in controlling adult *Bemisia tabaci* on peppers.
Figure 9:
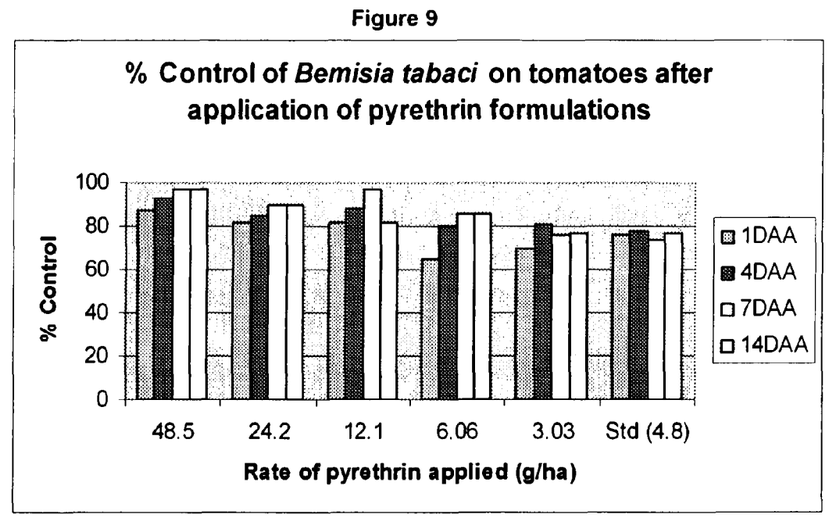
FIG. 9 is a graph showing the effect of the bio-insecticide/acaricide in controlling adult *Bemisia tabaci* on tomatoes.
Figure 10:
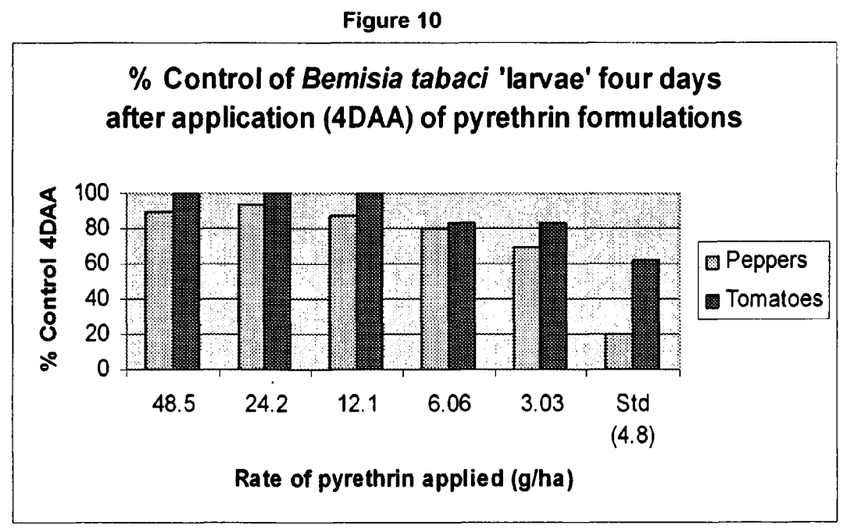
FIG. 10 is a graph showing the effect of the bio-insecticide/acaricide in controlling juvenile stages of *Bemisia tabaci* on two crops, 4 days after application (DAA)

Examples of results obtained with whitefly in Spain are shown in FIGS. 8 to 10. The efficacy of two EW formulations containing pyrethrins (25.2 g/l) plus dill seed oil is shown in Table 2 compared to the standard formulation containing pyrethrins (4%) plus piperonyl butoxide (16%)—Pelitre Hort.

TABLE 2

Control of adult whitefly on tomatoes following
the application of pyrethrin-containing formulations

| Treatment | Rate (g/ha of pyrethrins) | No.* 0 DAA | No. 1 DAA | No. 2 DAA | No. 4 DAA | No. 7 DAA | No. 14 DAA |
|---|---|---|---|---|---|---|---|
| Control | — | 35.0 | 38.8 | 36.8 | 34.5 | 28.8 | 27.8 |
| Formn A | 48.5 | 40.5 | 5.0 | 3.0 | 2.3 | 1.0 | 0.8 |
| Formn A | 24.2 | 53.3 | 7.0 | 5.8 | 5.3 | 2.8 | 2.8 |
| Formn A | 12.1 | 44.0 | 6.8 | 5.5 | 4.0 | 1.0 | 5.0 |
| Formn A | 6.06 | 50.5 | 13.5 | 9.8 | 7.0 | 4.0 | 4.0 |
| Formn A | 3.03 | 38.0 | 11.8 | 6.5 | 6.5 | 7.0 | 6.3 |
| Formn B | 48.5 | 45.0 | 1.8 | 1.8 | 2.0 | 1.5 | 1.0 |
| Formn B | 24.2 | 39.0 | 3.8 | 3.3 | 4.0 | 2.5 | 2.0 |
| Formn B | 12.1 | 45.3 | 7.3 | 5.8 | 5.3 | 2.5 | 3.0 |
| Formn B | 6.06 | 50.8 | 7.0 | 7.5 | 7.0 | 5.0 | 5.8 |
| Formn B | 3.03 | 37.5 | 9.3 | 8.8 | 9.5 | 7.5 | 6.0 |
| Pelitre Hort | 4.8 | 44.5 | 9.5 | 7.8 | 7.5 | 7.5 | 6.3 |

*No. of adults remaining (DAA = Days after application)

Figure 11:
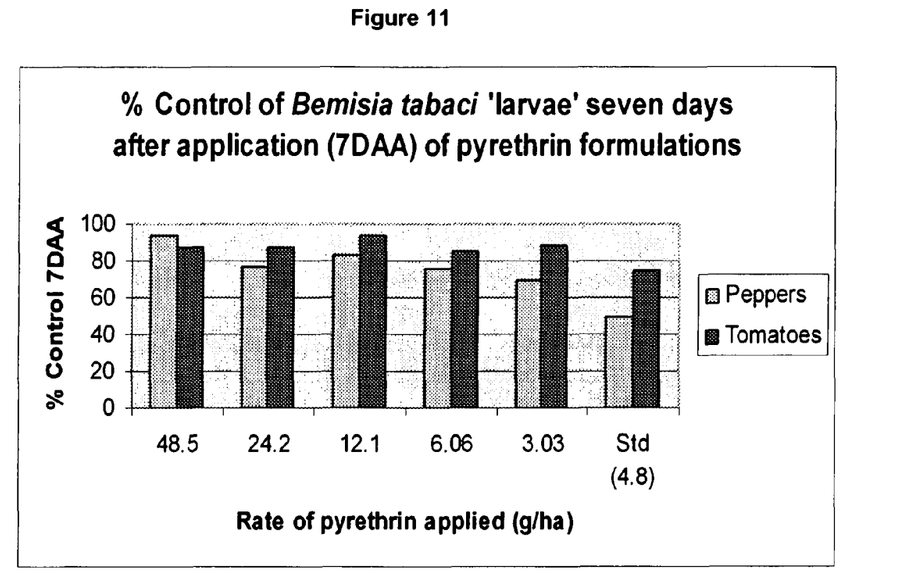
FIG. 11 is a graph showing the effect of the bio-insecticide/acaricide in controlling juvenile stages of *Bemisia tabaci* on two crops 7DAA.
Figure 12:
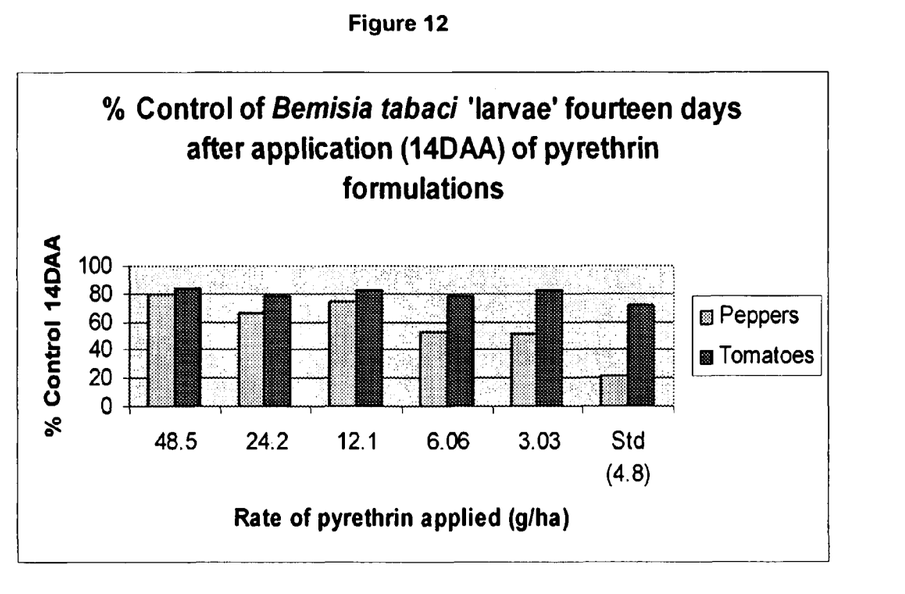
FIG. 12 is a graph showing the effect of the bio-insecticide/acaricide in controlling juvenile stages of *Bemisia tabaci* on two crops 14DAA.

Effectiveness in controlling adult whiteflies on peppers and tomatoes is shown in FIGS. 8 and 9, while efficacy against juvenile stages is displayed in FIGS. 10-12. Again the standard used was Pelitre Hort (pyrethrins plus piperonyl butoxide).

Thus, excellent control of both juvenile and adult stages of whitefly is provided by the pyrethrin/dill seed oil formulation. The control of adults is similar to the standard pyrethrin formulation used and for juveniles the improvement in control compared to that obtained with the standard is statistically significant. In addition, good control of aphids was obtained.

The invention claimed is:

1. A method for enhancing the effect of a pyrethin insecticide, comprising applying to a subject in need thereof a pyrethrin insecticide and an effective amount of dill oil as a potentiator for the insecticide, wherein the dill oil is Indian dill obtained from *Anethum sowa*.

2. A pesticidal composition which comprises a pyrethin insecticide and dill oil wherein the ratio of pyrethin insecticide:dill oil is in the range of from 1:5 to 5:1.

3. The pesticidal composition of claim 2, wherein the pyrethrin insecticide comprises pyrethrin.

4. The pestidicidal composition of claim 2, wherein the pyrethrin insecticide is a pyrethroid.

5. The pesticidal composition of claim 2, wherein the dill oil is Indian dill obtained from *Anethum sowa*.

6. The pesticidal composition of claim 2, wherein the dill oil is arranged in a rapid-release form, and the pesticide is arranged in a non-rapid release form.

7. The pesticidal composition of claim 2, wherein the composition further comprises a solvent.

8. The pesticidal composition of claim 2, wherein the dill oil is present in the composition in an amount of from about 5 to about 8% w/w.

9. The pesticidal composition of claim 8, wherein the dill oil is present in the composition in an amount of about 7.7% w/w.

10. A method for the control of pests which comprises administering to the pest or its environment in need thereof a pesticidally effective amount of a combination of dill oil and a pyrethin insecticide, wherein the dill oil is Indian dill obtained from *Anethum sowa*.

11. The method of claim 10 wherein the ratio of pyrethrin insecticide:dill oil is in the range of from 1:5 to 5:1.

12. A method for the control and/or eradication of pest infestations of animals and/or of plants, and/or stored products which comprises administering to the animal or locus in need thereof an effective amount of a combination of dill oil and a pyrethin insecticide, wherein the dill oil is Indian dill obtained from *Anethum sowa*.

13. The method of claim 12 wherein the ratio of pyrethrin insecticide:dill oil is in the range of from 1:5 to 5:1.

14. The pesticidal composition of claim 7 comprising ethyl lactate as the solvent.

* * * * *

UNITED STATES PATENT AND TRADEMARK OFFICE
CERTIFICATE OF CORRECTION

| | |
|---|---|
| PATENT NO. | : 8,137,715 B2 |
| APPLICATION NO. | : 12/375533 |
| DATED | : March 20, 2012 |
| INVENTOR(S) | : Sujay Anil Shah |

It is certified that error appears in the above-identified patent and that said Letters Patent is hereby corrected as shown below:

Column 7, lines 12-13: "Transfluthrin (2,3,5,6-tetrafluorobenzyl(1R,3S)-3-(2,2-dichlorovinyl)-2,12-dimethylcyclopropanecarboxylate)" should be
-- Transfluthrin (2,3,5,6-tetrafluorobenzyl(1R,3S)-3-(2,2-dichlorovinyl)-2,2-dimethylcyclopropanecarboxylate) --.

Signed and Sealed this
Seventh Day of August, 2012

David J. Kappos
*Director of the United States Patent and Trademark Office*